United States Patent
Jalali et al.

(10) Patent No.: US 8,521,267 B1
(45) Date of Patent: Aug. 27, 2013

(54) METHODS AND SYSTEMS FOR TRENDING ST SEGMENT CHANGES OVER TIME

(75) Inventors: Laleh Jalali, Moorpark, CA (US); Jay Snell, Studio City, CA (US); Elizabeth Bacon, Portland, OR (US); Katie Hoberman, S. Pasadena, CA (US); Bing Zhu, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 927 days.

(21) Appl. No.: 11/771,660

(22) Filed: Jun. 29, 2007

(51) Int. Cl.
*A61B 5/0472* (2006.01)

(52) U.S. Cl.
USPC .................................................. 600/516

(58) Field of Classification Search
USPC ............... 600/508–521; 607/525, 3, 17–21; 128/696
See application file for complete search history.

(56) References Cited

U.S. PATENT DOCUMENTS

| | | | | |
|---|---|---|---|---|
| 5,313,953 A * | 5/1994 | Yomtov et al. | 600/508 |
| 5,330,507 A * | 7/1994 | Schwartz | 607/14 |
| 5,520,191 A * | 5/1996 | Karlsson et al. | 600/515 |
| 6,112,116 A * | 8/2000 | Fischell et al. | 600/517 |
| 6,272,379 B1 * | 8/2001 | Fischell et al. | 607/5 |
| 6,609,023 B1 * | 8/2003 | Fischell et al. | 600/515 |
| 7,254,440 B1 * | 8/2007 | Kroll | 600/517 |
| 7,941,208 B2 * | 5/2011 | Sauer et al. | 600/518 |
| 2004/0122294 A1 * | 6/2004 | Hatlestad et al. | 600/300 |
| 2005/0113706 A1 * | 5/2005 | Prystowsky et al. | 600/518 |
| 2005/0137483 A1 * | 6/2005 | Fischell et al. | 600/509 |

* cited by examiner

*Primary Examiner* — Carl H Layno
*Assistant Examiner* — Paula J Stice
(74) *Attorney, Agent, or Firm* — Steven M Mitchell (57) ABSTRACT

A method and system are provided for trending a coronary burden such as an ischemic burden or acute myocardial infarction (AMI) for a patient. Trending provides obtaining cardiac data over a period of time, identifying the onset and the termination of coronary episodes based on a ST segment variation within the cardiac data, recording coronary burden information, and presenting the coronary burden information to a user. The coronary burden information may include the number of coronary episodes occurring over a period of time, the time duration of the coronary episodes, and the maximum ST segment variations for the coronary episodes that occur over a period of time.

22 Claims, 9 Drawing Sheets

Detection Log

| EGM | Type | Date | Time ▶ | Max ST Shift mV | HR Bin/Rate bpm | Duration M:S |
|---|---|---|---|---|---|---|
| 🗠 | AMI Detection | 12 May 2007 | 8:42 pm | -20 | Fast / 221 | 01:13 |
|  | Ischemia Burden | 11 May 2007 | 7:32 pm | -6 | Elevated 3 / 176 | 00:30 |
|  | Ischemia Burden | 2 May 2007 | 6:00 pm | -4 | Elevated 3 / 172 | 00:14 |
|  | Ischemia Burden | 29 Apr 2007 | 4:22 pm | -5 | Elevated 3 / 164 | 00:39 |
|  | Ischemia Burden | 29 Apr 2007 | 5:36 pm | 12 | Elevated 3 / 189 | 01:45 |
|  | Ischemia Burden | 22 Apr 2007 | 10:02 am | -18 | Fast / 211 | 01:55 |
|  | Ischemia Burden | 20 Apr 2007 | 8:13 am | -19 | Fast / 204 | 03:42 |
|  | Ischemia Burden | 14 Apr 2007 | 6:56 pm | -12 | Elevated 2 / 140 | 22:36 |
|  | Ischemia Burden | 3 Apr 2007 | 7:07 pm | 4 | Elevated 2 / 135 | 04:45 |
|  | Ischemia Burden | 2 Apr 2007 | 6:23 pm | -2 | Elevated 2 / 137 | 32:52 |
|  | Ischemia Burden | 30 Mar 2007 | 4:20 pm | -7 | Elevated 1 / 90 | 10:14 |
| 🗠 | Ischemia Burden | 28 Mar 2007 | 3:42 pm | -4 | Elevated 2 / 130 | 01:22 |

The first 16 and most recent 16 episodes since last cleared are listed.

32 Total

Last Session: 2 Mar 2007
Last Read: Today (2:41 pm)
Last Cleared: Today (2:45 pm)

METHODS AND SYSTEMS FOR TRENDING ST SEGMENT CHANGES OVER TIME

BACKGROUND OF THE INVENTION

Embodiments of the present invention pertain generally to implantable medical devices, and more particularly pertain to implantable and external medical devices that utilize ST segment variations within cardiac signals to record and present coronary burden information to illustrate trends.

An implantable medical device is implanted in a patient to monitor, among other things, electrical activity of a heart and to deliver appropriate electrical and/or drug therapy, as required. Implantable medical devices ("IMDs") include for example, pacemakers, cardioverters, defibrillators, implantable cardioverter defibrillators ("ICD"), and the like. The electrical therapy produced by an IMD may include, for example, pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm.

Cardiac ischemia is a condition whereby heart tissue does not receive adequate amounts of oxygen and is usually caused by a blockage of an artery leading to heart tissue. Ischemia arises during angina, acute myocardial infarction, coronary angioplasty, and any other condition that compromises blood flow to a region of tissue. When blockage of an artery is sufficiently severe, the cardiac ischemia becomes an acute myocardial infarction ("AMI") or also referred to as a myocardial infarction ("MI") or a heart attack. Ischemia and AMI represent related types of acute coronary burden.

Many patients at risk of cardiac ischemia have pacemakers, ICDs or other medical devices implanted therein. Electrocardiograms ("ECG") and intra-cardiac electrograms ("IEGM") are two types of cardiac signals that are very useful for diagnosing ischemia and locating damaged areas within the heart. Both ECGs and IEGMs comprise various waves and segments that represent heart depolarization and repolarization. The ST segment represents the portion of the cardiac signal between ventricular depolarization and ventricular repolarization. Variation, for example, elevation or depression in the voltage level (e.g., measured in millivolts, ADC counts or a percentage of ST shift, and the like) of the ST segment in an ECG or IEGM may result when there are abnormalities in the polarization of cardiac tissue during an acute coronary episode such as an ischemia or an acute myocardial infraction (AMI).

Techniques have been developed for detecting cardiac ischemia using implanted medical devices. However, coronary episodes (e.g. ischemias) may occur sporadically occurring sometimes once in a few weeks or other times occurring many times in a day. Today, external programmers exist that communicate wirelessly or via telemetry with the IMD and download, from the IMD, a limited amount of information related to a coronary event. For example, conventional programmers notify a physician that a coronary event has occurred and the time at which the event started. The programmers also allow a physician to view the IEGM signal at the onset of the coronary event. Today, IMDs process coronary events as a triggering type event that directs the IMD to take an action such as to save, in long-term memory, the IEGM signal as well as other information such as patient status associated with the event.

However, conventional approaches to ischemic events have not satisfactorily captured the various types of information that characterize an ischemic episode. Nor have conventional approaches been able to record and present long-term ischemia related burden information and the trends associated therewith. A need remains for improved methods and systems for trending acute coronary burden based on ST segment variations.

SUMMARY

In accordance with at least one embodiment, a method is provided for trending coronary burden for a patient that provides obtaining cardiac data over a period of time, identifying the onset and the termination of coronary episodes based on a ST segment variation within the cardiac data, recording coronary burden information, and presenting the coronary burden information to illustrate trends. The coronary burden information including a count of the coronary episodes over the period of time, time durations of the coronary episodes, and maximum ST segment variations for the coronary episodes over the period of time.

Optionally, the method may provide a detection log for storing: i) the most recent ischemic episodes; ii) the most recent AMI episodes; iii) the highest ST segment variation; iv) the longest ST segment variation; v) an episode type, and vi) a heart rate bin and an average heart rate at onset of the ischemic episode. In addition to presenting trend information, the method may include displaying an IEGM signal at a time of a coronary episode, co-displaying baseline ST segment variation over a baseline period of time and the coronary burden information, displaying a graphical representation of the coronary burden information, displaying over time, a percentage of time that coronary episodes occurred per unit of time, and displaying over time, the count of coronary episodes that occurred per unit of time.

In accordance with another embodiment, a system for trending coronary burden for a patient. The system includes a processor to obtain cardiac data over a period of time and to identify an onset and a termination of coronary episodes based on ST segment variation within the cardiac data. Memory records coronary burden information over the period of time. The coronary burden information includes at least one of: i) a count of the coronary episodes over the period of time; ii) time durations of the coronary episodes; iii) maximum ST segment variations for the coronary episodes over the period of time. A display presents the coronary burden information to illustrate trends.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

Figure 1:
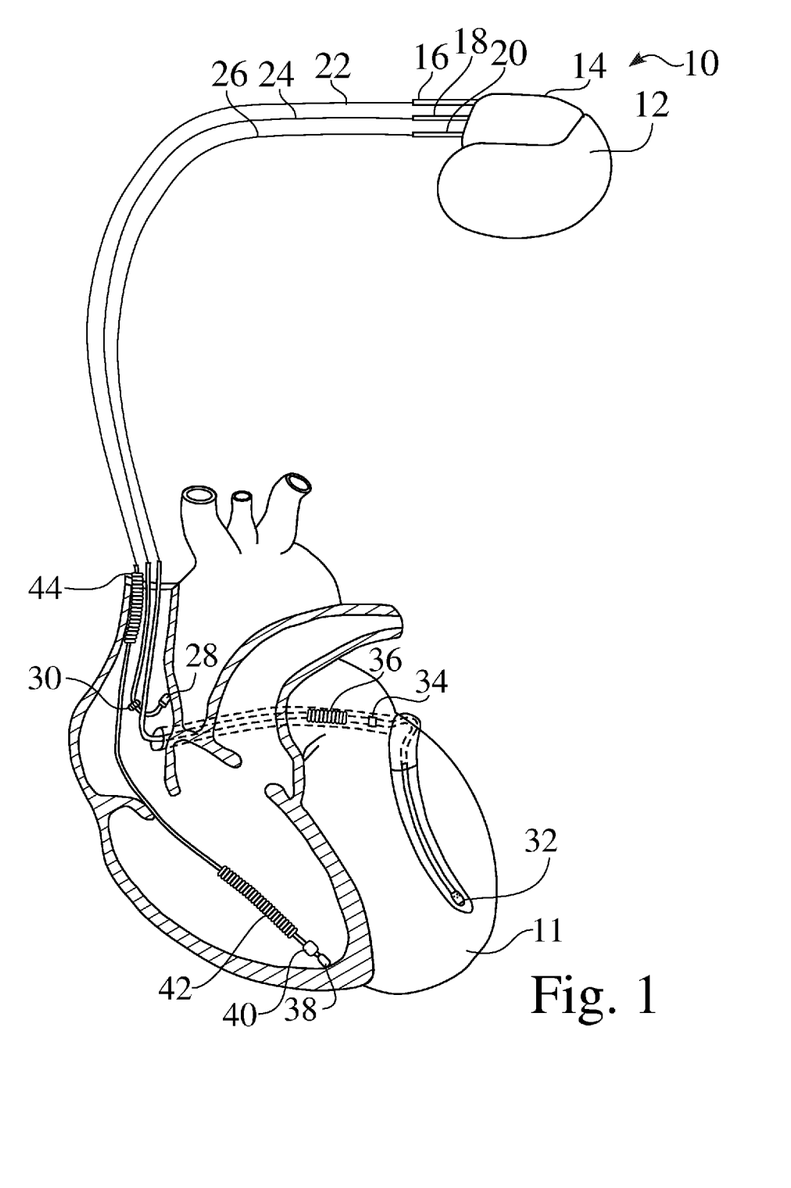
FIG. 1 illustrates an implantable medical device formed in accordance with an embodiment of the present invention.

FIG. 1 illustrates an implantable medical device 10 (IMD) that is coupled to a heart 11. The implantable medical device 10 may be a cardiac pacemaker, an implantable cardioverter defibrillator ("ICD"), a defibrillator, or an ICD coupled with a pacemaker implemented in accordance with an embodiment of the present invention. The IMD 10 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. As explained below in more detail, the IMD 10 may be controlled to monitor cardiac signals and based thereof, to identify potentially abnormal physiology (e.g., ischemia). The detected cardiac signals may include intrinsic heart beats that have no assistance from any type of manmade electrical stimulation. Alternatively, the detected cardiac signals may include heart beats that have been stimulated by an electrical source to produce a paced heartbeat. The electrical source that provides the paced heartbeat may include an implantable device that provides low energy electrical signals, such as provided by a pacemaker, a demand pacemaker, a single-chamber pacemaker, a dual chamber pacemaker, a biventricular pacemakers and the like. Optionally, the paced heartbeat may be generated by an implantable device that provides high energy electrical signals such as those provided by an implantable cardioverter defibrillator.

The IMD 10 includes a housing 12 that is joined to a header assembly 14 (e.g., an IS-4 connector assembly) that holds receptacle connectors 16, 18, and 20 that are connected to a right ventricular lead 22, a right atrial lead 24, and a coronary sinus lead 26, respectively. The leads 22, 24 and 26 may be located at various locations, such as an atrium, a ventricle, or a combination of both to measure the physiological condition of the heart 11. One or more of the leads 22, 24 and 26 detect intra-cardiac electrogram (IEGM) signals that form an electrical activity indicator of myocardial function over multiple cardiac cycles. To sense atrial cardiac signals and to provide right atrial chamber stimulation therapy, the right atrial lead 24 having at least an atrial tip electrode 28, which is typically implanted in the right atrial appendage, and an atrial ring electrode 30. The IEGM signals represent analog signals that are subsequently digitized and analyzed to identify waveforms of interest. Examples of waveforms identified from the IEGM signals include the P-wave, T-wave, the R-wave, the QRS complex and the like. The waveforms of interest may be collected over a period of time, either continuously or at defined intervals.

The coronary sinus lead 26 receives atrial and ventricular cardiac signals and delivers left ventricular pacing therapy using at least a left ventricular tip electrode 32, left atrial pacing therapy using at least a left atrial ring electrode 34, and shocking therapy using at least a left atrial coil electrode 36. The right ventricular lead 22 has a right ventricular tip electrode 38, a right ventricular ring electrode 40, a right ventricular (RV) coil electrode 42, and a SVC coil electrode 44. Therefore, the right ventricular lead 22 is capable of receiving cardiac signals, and delivering stimulation in the form of pacing and shock therapy to the right ventricle.

Figure 2:
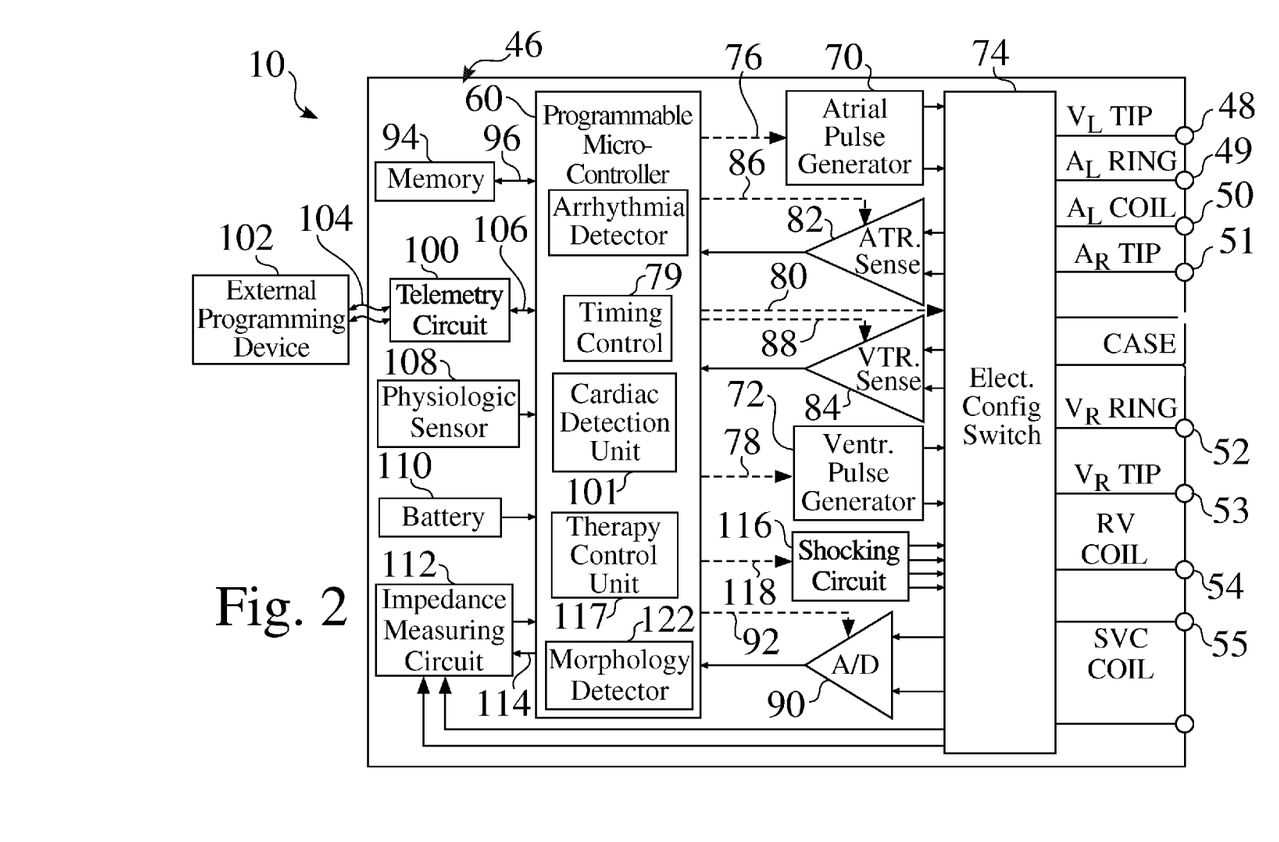
FIG. 2 illustrates a functional block diagram of exemplary internal components of an implantable medical device formed in accordance with an embodiment of the present invention.

FIG. 2 illustrates a block diagram of exemplary internal components of the IMD 10. The IMD 10 is for illustration purposes only, and it is understood that the circuitry could be duplicated, eliminated or disabled in any desired combination to provide a device capable of treating the appropriate chamber(s) of the heart with cardioversion, defibrillation and/or pacing stimulation.

The housing 46 for IMD 10 (shown schematically in FIG. 2), is often referred to as the "can", "case" or "case electrode" and may be programmably selected to act as the return electrode for all "unipolar" modes. The housing 46 further includes a connector (not shown) having a plurality of terminals, namely a right atrial tip terminal ($A_R$ TIP) 51, a left ventricular tip terminal ($V_L$ TIP) 48, a left atrial ring terminal ($A_L$ RING) 49, a left atrial shocking terminal ($A_L$ COIL) 50, a right ventricular tip terminal ($V_R$ TIP) 53, a right ventricular ring terminal ($V_R$ RING) 52, a right ventricular shocking terminal ($R_V$ COIL) 54, and an SVC shocking terminal (SVC COIL) 55.

The IMD 10 includes a programmable microcontroller 60, which controls the operation of the IMD 10 based on acquired cardiac signals. For example, the microcontroller 60 includes a cardiac detection unit 101 to monitor the cardiac signals and to identify therein ST segment shifts and determine potential ischemic and AMI conditions. The microcontroller 60 (also referred to herein as a processor module or unit) typically includes a microprocessor, or equivalent control circuitry, is designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (e.g., data) as controlled by a program code stored in memory. Among other things, the microcontroller 60 receives, processes, and manages storage of digitized data from the various electrodes. The microcontroller 60 may also analyze the data, for example, in connection with collecting, over a period of time, reference ST segment shifts in a cardiac signal (e.g., sense signals received from leads 22, 24 and 26). As explained below in connection with FIGS. 4-6, the microcontroller 60 obtains a ST threshold by statistically determining variability in the ST segment shift based on reference ST segment shifts. The microcontroller 60 may also measure ST segment shifts and compares them to the ST threshold to identify a potential abnormal physiology (e.g., such as when the patient is having a post-myocardial infarct, a "silent" myocardial infarct, a myocardial infarct, an ischemia, a heart block, an arrhythmia, fibrillation, congestive heart failure, and the like).

The IMD 10 includes an atrial pulse generator 70 and a ventricular/impedance pulse generator 72 to generate pacing stimulation pulses. In order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

Switch 74 includes a plurality of switches for connecting the desired electrodes to the appropriate I/O circuits, thereby providing complete electrode programmability. Atrial sensing circuits 82 and ventricular sensing circuits 84 may also be selectively coupled to the leads through the switch 74 for detecting the presence of cardiac activity in each of the four chambers of the heart. Control signals 86 and 88 from processor 60 direct output of the atrial and ventricular sensing circuits, 82 and 84, that are connected to the microcontroller 60. In this manner, the atrial and ventricular sensing circuits, 82 and 84 are able to trigger or inhibit the atrial and ventricular pulse generators, 70 and 72.

The cardiac signals are applied to the inputs of an analog-to-digital (A/D) data acquisition system 90. The data acquisition system 90 is configured to acquire IEGM signals, convert the raw analog data into a digital IEGM signals, and store the digital IEGM signals in memory 94 for later processing and/or telemetric transmission to an external device 102. Memory 94 may also store a variable threshold value 120 and a ST threshold 122 (shown in FIG. 2B). Control signal 92 from processor 60 determines when the ND 90 acquires signals, stores them in memory 94, or transmits data to an external device 102. The data acquisition system 90 is coupled to the right atrial lead 24, the coronary sinus lead 26, and the right ventricular lead 22 through the switch 74 to sample cardiac signals across any combination of desired electrodes.

The cardiac detection unit 101 receives the cardiac signals from ND 90 and determines the onset and determination of an ischemic or AMI condition based on ST segment shifts. The ST segment may include variations of ST segments that occur over a period of time. The onset of ischemia may be determined by the cardiac detection unit 101 by using a statistical determination of the variability of the ST segment shift. For example, a plurality of ST segment shifts may be collected to obtain a ST threshold. Then the ST threshold is used in a comparison with subsequently measured ST segment shifts to identify the onset of a coronary episode. When the measured ST segment shift is less than a ST threshold, the termination of the coronary episode is identified. Upon detecting the onset of a coronary episode, either an ischemic event or an AMI event, the cardiac signals (e.g., IEGM or EGM) are stored in memory 94.

The microcontroller 60 is coupled to the memory 94 by a suitable data/address bus 96, wherein the programmable operating parameters used by the microcontroller 60 are stored and modified, as required, in order to customize the operation of IMD 10 to suit the needs of a particular patient. The memory 94 may also store data indicative of myocardial function, such as the IEGM data, ST segment shifts, reference ST segment shifts, and ST segment shift thresholds and the like for a desired period of time (e.g., one hour, 24 hours, one month, and the like). In addition, the memory 94 may store data for each time a shift of the ST segment is detected that exceeds a predetermined threshold.

Memory 94 may also store large amounts of data in order to determine an ischemic burden, an AMI burden and to determine trends. Each occurrence of an ischemic event or AMI condition that occurs in a patient over a year period of time may be stored in memory 94. In addition, the cardiac signals are categorized according to their heart rate in beats per minute (bpm) and placed in heart rate bins for additional processing. Therefore, the categorization of each cardiac signal may be also stored in memory 94. Furthermore, memory 94 may store statistical parameters based on ST segment shifts (e.g. an average, a standard deviation, and the like). Thus, memory 94 may store all the information necessary to present ischemic burden, AMI burden and trend information to a user, such as shown in FIGS. 6-9. The memory 94 may also store instructions that direct the microcontroller 60 to analyze the data to detect ischemia and/or to identify events of interest.

The operating parameters of the IMD 10 may be non-invasively programmed into the memory 94 through a telemetry circuit 100 in communication with the external device 102, such as a programmer (shown in FIG. 3), trans-telephonic transceiver or a diagnostic system analyzer. The telemetry circuit 100 is activated by the microcontroller 60 by a control signal 106. The telemetry circuit 100 allows intracardiac electrograms, and status information relating to the operation of IMD 10 (as contained in the microcontroller 60 or memory 94) to be sent to the external device 102 through an established communication link 104.

The IMD 10 additionally includes a battery 110, which provides operating power to all of the circuits shown within the housing 46, including the processor 60. The IMD 10 is shown as having an impedance measuring circuit 112 which is enabled by the microcontroller 60 via a control signal 114. The impedance measuring circuit 112 is advantageously coupled to the switch 74 so that impedance at any desired electrode may be obtained.

In the case where IMD 10 is intended to operate as an implantable cardioverter/defibrillator (ISCD) device, the IMD 10 detects the occurrence of an ST segment shift that indicates an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (e.g., up to 0.5 joules), moderate (e.g., 0.5-10 joules) or high energy (e.g., 11 to 40 joules), as controlled by the microcontroller 60. Such shocking pulses are applied to the heart 11 of the patient through at least two shocking electrodes, and as shown in this embodiment, selected from the left atrial coil electrode 36, the RV coil electrode 42, and/or the SVC coil electrode 44.

Figure 3:
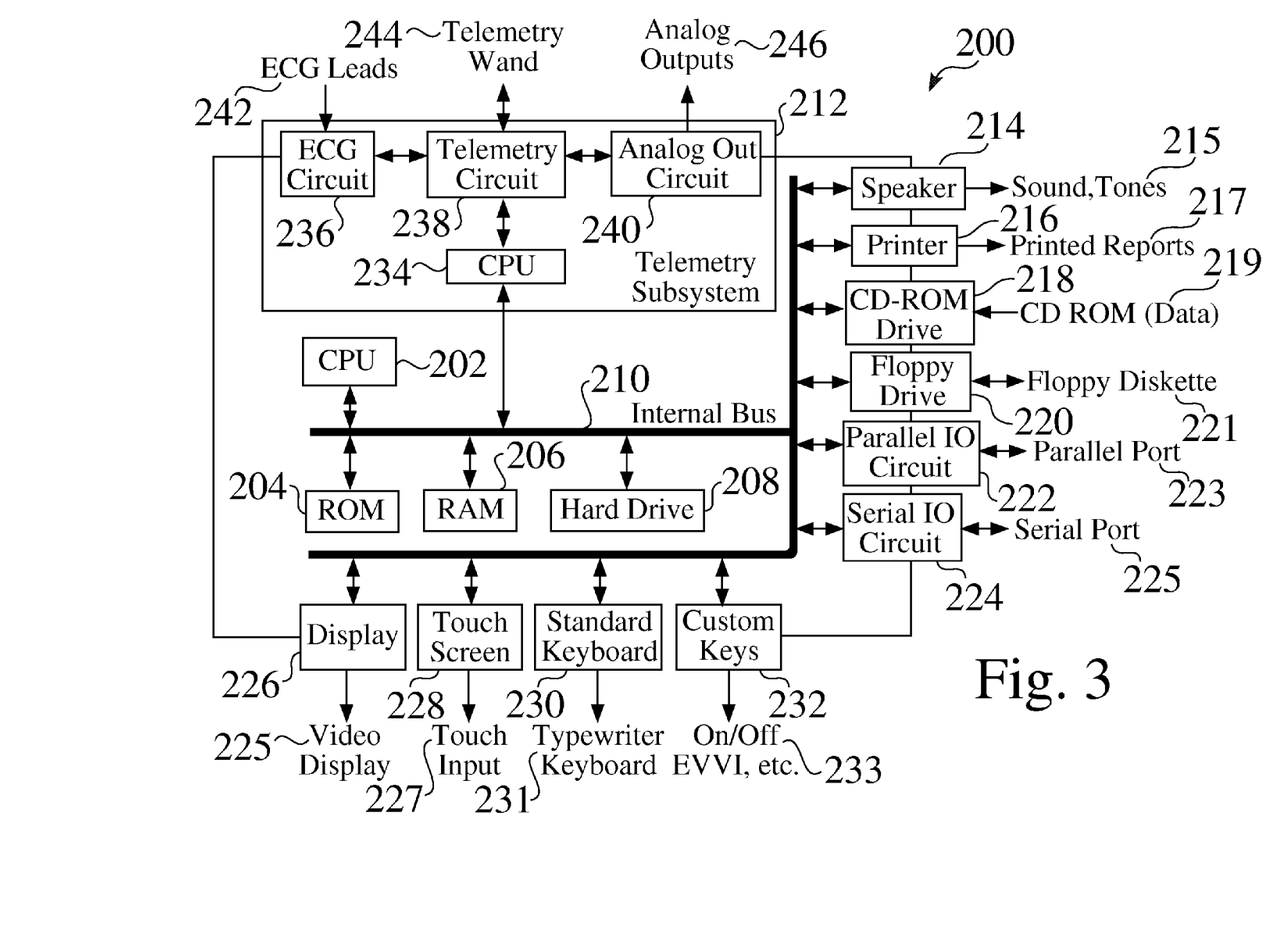
FIG. 3 illustrates a functional block diagram of certain components of an external programmer used to communicate with the implantable medical device shown in FIG. 1 utilized in accordance with an embodiment of the present invention.

FIG. 3 illustrates a functional block diagram of an external device 200, such as a programmer, that is operated by a physician, a health care worker, or a patient to interface with IMD 10. The external device 200 may be utilized in a hospital setting, a physician's office, or even the patient's home to communicate with the IMD 10 to change a variety of operational parameters regarding the therapy provided by the IMD 10 as well as to select among physiological parameters to be monitored and recorded by the IMD 10. Further, the external device 200 may be utilized to interrogate the IMD 10 to determine the condition of a patient, to adjust the physiological parameters monitored, or to adapt the therapy to a more efficacious one in a non-invasive manner.

External device 200 includes an internal bus 210 that connects/interfaces with a Central Processing Unit (CPU) 202, ROM 204, RAM 206, a hard drive 208, a speaker 214, a printer 216, a CD-ROM drive 218, a floppy drive 220, a parallel I/O circuit 222, a serial I/O circuit 224, a display 226, a touch screen 228, a standard keyboard connection 230, custom keys 232, and a telemetry subsystem 212. The internal bus 210 is an address/data bus that transfers information (e.g., either memory data or a memory address from which data will be either stored or retrieved) between the various components described. The hard drive 208 may store operational programs as well as data, such as reference ST segments, ST thresholds, timing information and the like.

The CPU 202 typically includes a microprocessor, a microcontroller, or equivalent control circuitry, designed specifically for controlling interfacing the external device 200 with the IMD 10. The CPU 202 may further include RAM or ROM memory, logic and timing circuitry, state machine circuitry, and I/O circuitry to interface with the IMD 10. Typically, the microcontroller 60 includes the ability to process or monitor input signals (data) as controlled by program code stored in memory (e.g., ROM 206).

In order for a physician or health care worker to communicate with the external device 200, a display 226, a touch screen 228, a standard keyboard 230, and custom keys 232 are provided. The display 226 (e.g., may be connected to a video display 225) and the touch screen 228 display text, alphanumeric information, data and graphic information via a series of menu choices to be selected by the user relating to the IMD 10, such as for example, status information, operating parameters, therapy parameters, patient status, access settings, software programming version, ST segment thresholds, and the like. The display 226 may present trending information, such as shown in the screenshots of FIGS. 6-9. The touch screen 228 accepts a user's touch input 227 when selections are made. The keyboard 230 (e.g., a typewriter keyboard 231) allows the user to enter data as well as interface with the telemetry subsystem 212.

Furthermore, custom keys 232 turn on/off 233 the external device 200, a printer 216 prints hard-copies of any reports 217 for a physician/healthcare worker to review or to be placed in a patient file, and speaker 214 provides an audible warning (e.g. sounds and tones 215) to the user in the event any abnormal situations occur while the external device 200 is being used. In addition, the external device 200 includes a parallel I/O circuit 222 to interface with a parallel port 223, a serial I/O circuit 224 to interface with a serial port 225, a floppy drive 220 to accept floppy diskettes 221, and a CD-ROM drive 218 that accepts CD ROMs 219.

The telemetry subsystem 212 includes a central processing unit (CPU) 234 in electrical communication with a telemetry circuit 238, which communicates with both an ECG circuit 236 and an analog out circuit 240. The ECG circuit 236 is connected to ECG leads 242, the telemetry circuit 238 is connected to a telemetry wand 244, and the analog out circuit 212 includes communication circuits, such as a transmitting antenna, modulation and demodulation stages (not shown), as well as transmitting and receiving stages (not shown) to communicate with analog outputs 246. The external device 200 may wirelessly communicate with the IMD 10 and utilize protocols, such as Bluetooth, GSM, infrared wireless LANs, HIPERLAN, 3G, satellite, as well as circuit and packet data protocols, and the like. The wireless RF link utilizes a carrier signal that is selected to be safe for physiologic transmission through a human being and is below the frequencies associated with wireless radio frequency transmission. Alternatively, a hard-wired connection may be used to connect the external device 200 to IMD 10 (e.g., an electrical cable having a USB connection).

Figure 4:
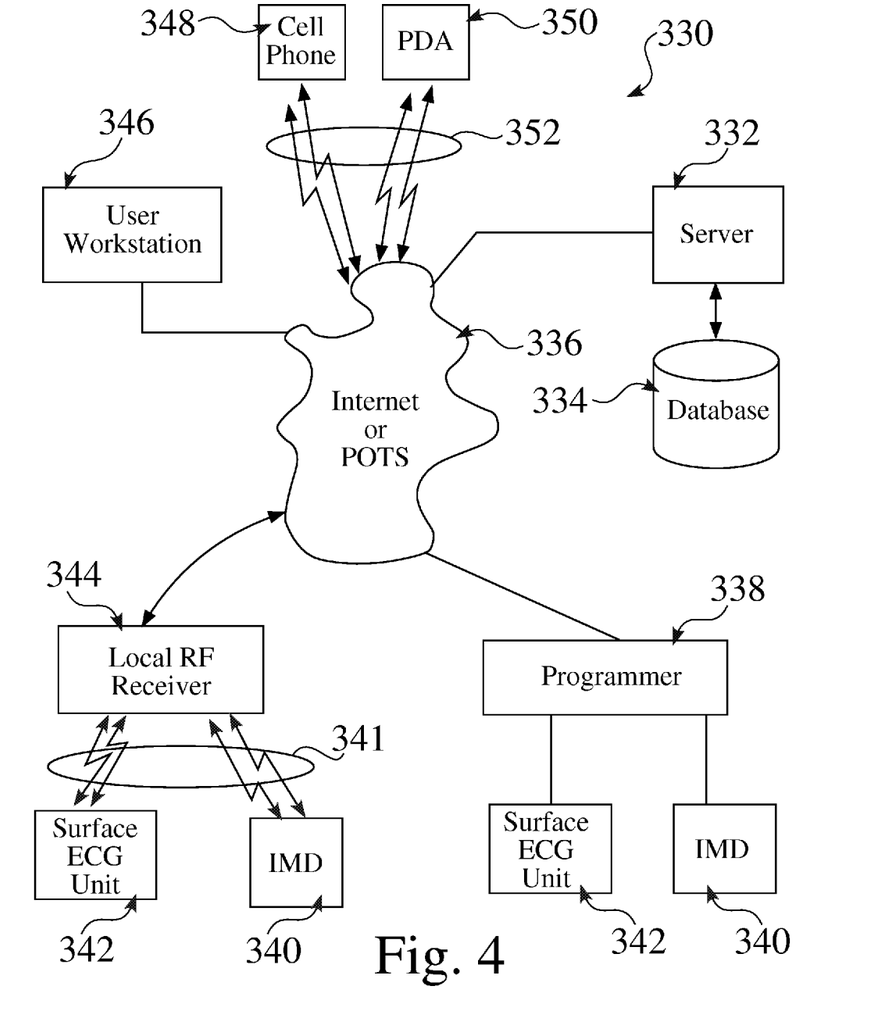
FIG. 4 illustrates a functional block diagram of a distributed processing system in accordance with an embodiment of the present invention.

FIG. 4 illustrates a distributed processing system 330 in accordance with an embodiment of this invention. The distributed processing system 330 includes a server 332 that is connected to a database 334, a programmer 338 (e.g. similar to external device 200 described above), a local RF transceiver 334 and a user workstation 346 electrically connected to a communication system 336 such as the internet, a voice over IP ("VoIP") gateway, or a local plain old telephone service ("POTS") such as a public switched telephone network ("PSTN"). Alternatively, the communication system 336 may be a local area network ("LAN"), a campus area network ("CAN"), a metropolitan area network ("MAN"), or a wide area network ("WAM"). The communication system 336 serves to provide a network that facilitates the transfer/receipt of cardiac signals, processed cardiac signals, histograms, trend analysis and patient status, and the like.

The server 332 is a computer system that provides services to other computing systems (e.g., clients) over a computer network. The server 332 acts to control the transmission and reception of information (e.g., cardiac signals, processed cardiac signals, ST segments, histograms, statistical analysis, trend lines, and the like). The server 332 interfaces with a communication system 336, such as the internet or a local POTS based telephone system, to transfer information between the programmer 338, the local RF transceiver 344, the user workstation as well as a cell phone 348, and a personal data assistant ("PDA") 350 to the database 334 for storage/retrieval of records of information. For instance, the server 332 may download to a cell phone 348 or PDA 350 the results of processed cardiac signals, ST segment trends, or a patient's physiological state (e.g., is the patient having or has had an ischemia) based on previously recorded cardiac information. ST segment trends may include variations of ST segments occurring over a period of time. On the other hand, the server 332 may upload raw cardiac signals (e.g., unprocessed cardiac data) from surface ECG unit 342 or IMD 340 via the local RF transceiver 344 or the programmer 338.

Database 334 is any commercially available database that stores information in a record format in electronic memory. The database 334 stores information such as raw cardiac data, processed cardiac signals, statistical calculations (e.g., averages, modes, standard deviations), histograms, coronary burden information, cardiac trends (e.g., ST segment trends), and the like. The information is downloaded into the database 334 via the server 332 or, alternatively, the information is uploaded to the server from the database 334.

The programmer 338 is similar to the programmer 200 described above and may reside in a patient's home, a hospital, or a physician's office. Programmer 338 interfaces with a surface ECG unit 342 and an IMD 340 (e.g., similar to ICD 10 described above). The programmer 338 may wirelessly communicate with the IMD 340 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 338 to IMD 10 (e.g., an electrical cable having a USB connection). The programmer 338 is able to acquire cardiac signals from the surface of a person (e.g., ECGs), or the programmer is able to acquire intra-cardiac electrograms (e.g., IEGMs) from IMD 340. The programmer 338 interfaces with the communication system 336, either via the internet or via POTS, to upload the cardiac data acquired from the surface ECG unit 342 or the IMD 340 to the server 332. The programmer 338 may upload more than just raw cardiac data. For instance, the programmer 338 may upload status information, operating parameters, therapy parameters, patient status, preference settings, software programming version, ST segment thresholds, and the like.

The local RF transceiver 334 interfaces with the communication system 336, either via the internet or via POTS, to upload cardiac data acquired from the surface ECG unit 342 or the IMD 340 to the server 332. In one embodiment, the surface ECG unit 342 and the IMD 340 have a bi-directional connection with the local RF transceiver via a wireless connection 341. The local RF transceiver 344 is able to acquire cardiac signals from the surface of a person (e.g., ECGs), or acquire intra-cardiac electrogram (e.g., IEGM) from IMD 340. On the other hand, the local RF transceiver 344 may download stored cardiac data from database 334 or the analysis of cardiac signals from database 334 (e.g., ST segment statistical analysis, ST segment trends, and the like) information to the surface ECG unit 342 or IMD 340.

The user workstation 346 may interface with the communication system 336 via the internet or POTS to download information via the server 332 from the database 334. Alternatively, the user workstation may download raw data from the surface ECG unit 342 or IMD 340 via either the programmer 338 or the local RF transceiver 344. Once the user workstation 346 has downloaded the cardiac information (e.g., raw cardiac signals, ST segments, and the like), the user workstation 346 may process the cardiac signals, create histograms, calculate statistical parameters, or determine cardiac trends and determine if the patient is suffering from ischemia or another physiological condition. Once the user workstation 346 has finished performing its calculations, the user workstation 346 may either download the results to the cell phone 348, the PDA 350, the local RF transceiver 344, the programmer 338, or to the server 332 to be stored on the database 334. Both programmer 338 and workstation 346 may present coronary burden information to illustrate trends. The trends may be displayed in screenshots (as shown in FIGS. 6-9).

Figure 5:
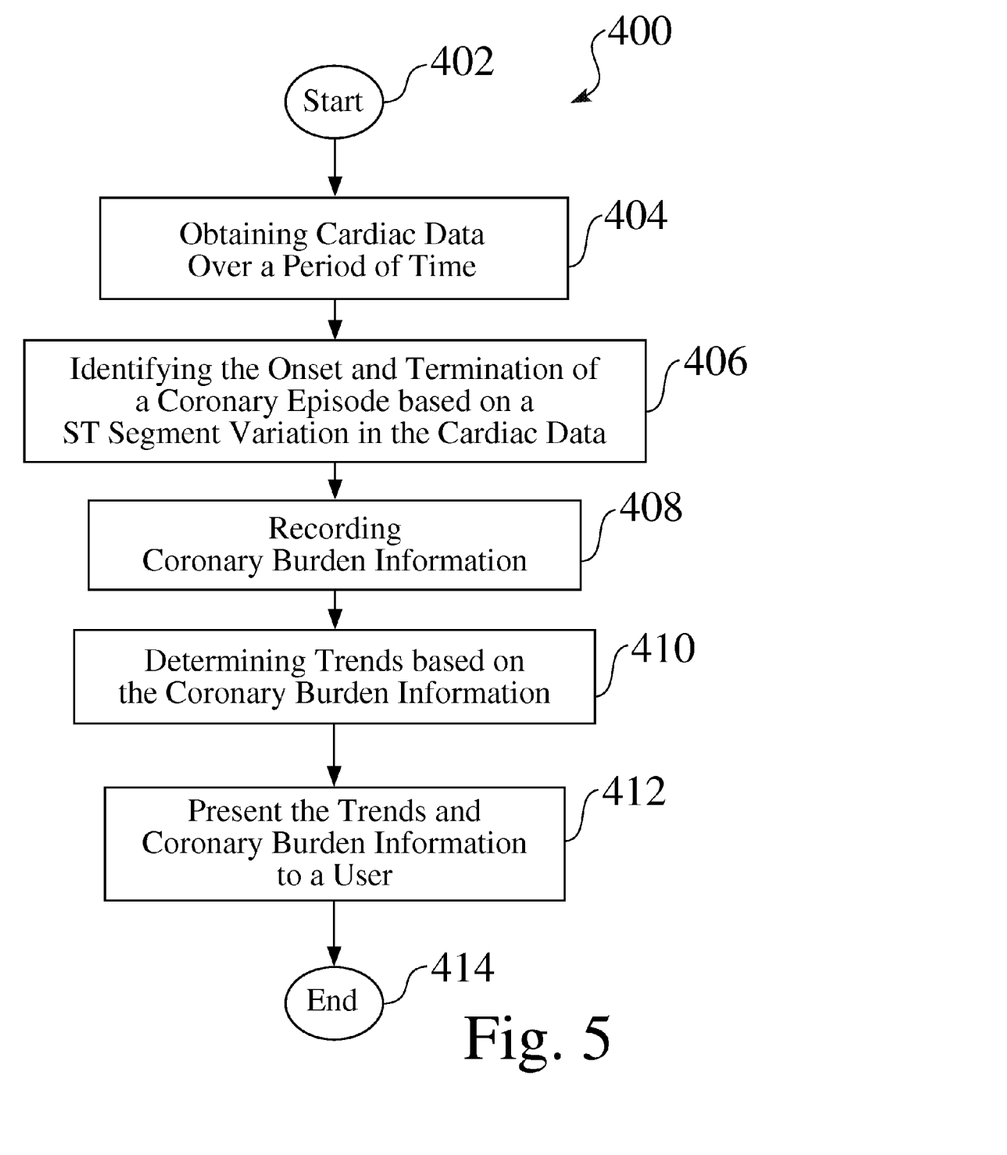
FIG. 5 illustrates a flow diagram for recording presenting trends and coronary burden information to a user in accordance with an embodiment of the present invention.

FIG. 5 illustrates a flow chart 400 that depicts a process for recording and presenting trends and coronary burden information to a user in accordance with an embodiment of the present invention. At 402, the process commences.

At 404, cardiac data is obtained over a period of time (e.g., over multiple cardiac cycles). The cardiac data may be cardiac signals that represent intra-cardiac electrogram (IEGM) signals, electrocardiogram (ECG) signals and the like. Furthermore, the cardiac signals may be raw cardiac signals (e.g. ECG or IEGMs), processed cardiac signals (e.g. ST segment shifts), and the like. The cardiac cycle is composed of a p-wave, a Q-wave, an R-wave, an S-wave, and a T-wave. The portion of the signal between the S-wave and T-wave constitutes a ST segment. The ST segment may have a voltage level that aligns with the voltage level of a baseline heart rhythm. Alternatively, the ST segment may have a voltage level that is shifted above or shifted below the baseline. ST segment variations indicate a potential coronary episode. ST segment variations may include ST deviations or ST shifts.

A ST deviation is determined by subtracting an average PQ segment (e.g., the isoelectric segment) voltage from the ST segment voltage for a heartbeat. The ST deviation provides a measure of the change in variability over a period of time. An ST shift is determined by changes in the ST deviation over a period of time. For example, the current ST shift is calculated by subtracting a stored baseline ST deviation from a new acquired ST deviation. Deviations of the voltage level of the ST segment may be a result of injury to cardiac muscle, changes in the synchronization of ventricular muscle depolarization, drug or electrolyte influences, and the like. Thus, ST segment variations are a reliable indicator of the possibility of a coronary episode, such as an ischemia or an acute myocardial infarction.

At 406, the ST segment variation of the cardiac signal is analyzed to identify the onset of a coronary episode and the termination of a coronary episode. Not all variations in ST segment are potential coronary episodes. A shift in the ST segment can be caused by non-ischemia related factors, such as "axis shifts", electrical noise, cardiac pacing, high sinus or tachycardia cardiac rates that distort the cardiac signal. The measured ST segments may include noise. Upon extracting the ST segment from the noise it is possible to discriminate the occurrence of a coronary episode. The discrimination of ischemia related and non-ischemia related shifts in the ST segment may be achieved through a statistical determination of the variability of the ST segment shift. A plurality of ST segment shifts are collected to obtain a ST threshold. Then the ST threshold is used in a comparison with subsequently measured ST segment shifts to identify the onset of a coronary episode. When the measured ST segment shift is less than a ST threshold, the termination of the coronary episode is identified. Upon detecting the onset of a coronary episode, either an ischemic event or an AMI event, the cardiac signals (e.g., IEGM or EGM) are stored in memory 94.

At 408, coronary burden information is recorded, e.g. stored in memory 94 within the ICD 10. Coronary burden information includes the number of coronary episodes that occur over a selected time period and the duration of each episode during that time period. Coronary burden information provides a physician or health care worker a measure of the burden placed on a patient's heart over the period of time. The coronary burden information may include a detection log storing the most recent ischemic episodes; the most recent AMI episodes; the highest ST segment variation; the longest ST segment variation; an episode type (e.g., including both major and minor ST elevation and depression), a heart rate bin and an average heart rate at the onset of the coronary episode and the like.

At 410, coronary trends are determined based on the coronary burden information. A trend utilizes the coronary burden to provide a physician with the ability to assess the existence, exacerbation and/or alleviation of a coronary episode, such as a myocardial ischemia or AMI. Trends may provide the time duration a patient spent with an ischemic burden or AMI burden, the duration and the number of episodes of ischemia or AMI, as well as the maximum ST shift episodes associated with the coronary episodes.

At 412, the trends and coronary burden information are presented to the user. Presenting may be performed by displaying the coronary burden information in a graphical (e.g., a CRT display, a LCD display, or any type of GUI) display or in any printed medium, and/or providing an audio representation thereof. Presenting includes displaying a graphical representation of the coronary burden information, displaying an IEGM signal at a time of a coronary episode, co-displaying a baseline ST segment variation over a baseline period of time, as well as displaying, over time, a percentage of time that coronary episodes occurred per unit of time and the count of coronary episodes that occurred per unit of time. At 414, the process terminates and may be repeated.

FIGS. 6-9 illustrate exemplary formats and types of characteristics to present trends in coronary burden information and the underlying coronary burden information.

Figure 6:
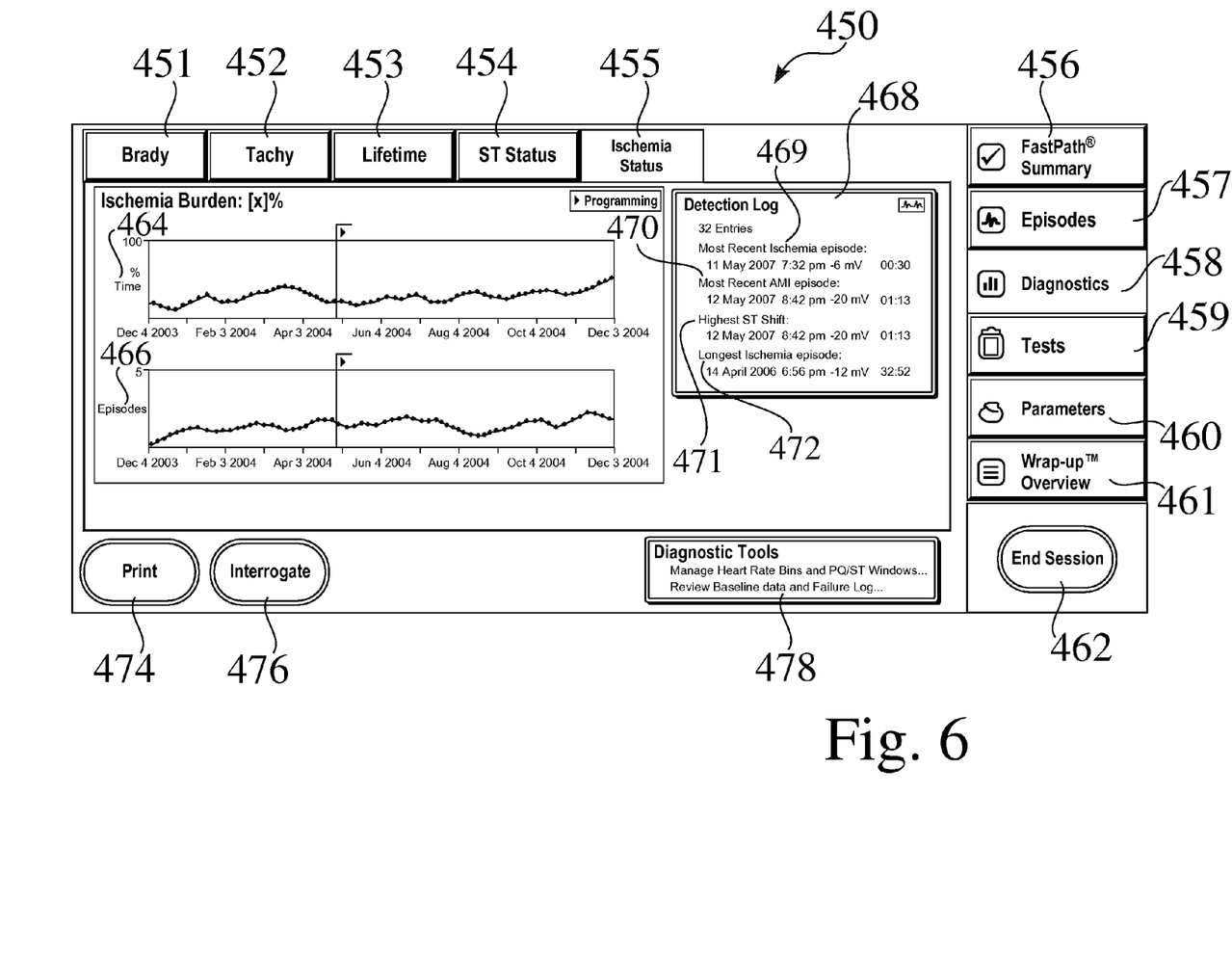
FIG. 6 illustrates a screen shot depicting a coronary episode log utilized to present trends in accordance with an embodiment of the present invention.

FIG. 6 illustrates a screen shot 450 depicting a coronary episode log in accordance with an embodiment of the present invention. The screen shot 450 includes buttons to select for brady 451, tachy 452, lifetime 453, ST status 454, and ischemia status 455, a fastpath summary 456, episodes 457, diagnostics 458, tests 459, parameters 460, wrap-up overview 461 and an end of session 462. Further, screen shot 450 has graphs that display the percent of time 464 a person is in a coronary episode and the number of episodes 466 a person has over a period of time. A detection log 468 is provided that lists the most recent entries (e.g., thirty-two) of coronary episodes. Alternatively, other amounts for entries may be included (e.g., five entries, ten entries, twenty entries, thirty entries, fifty entries, one-hundred entries and the like). For instance, the detection log may contain the most recent ischemia episode 469, the most recent AMI episode 470, the highest ST shift 471, and the longest ischemia episode 472. In addition, a user may select a print 474 button to print the display of the percent print of time 464, the number of episodes 466 or the detection log 468. The user may select to interrogate 476 a particular coronary episode, or run diagnostic tools 478. If the user selects to activate the detection log 468, a new screen shot (shown in FIG. 7) depicting a list of all the most recent entries of coronary episodes stored in memory will be displayed.

Figure 7:
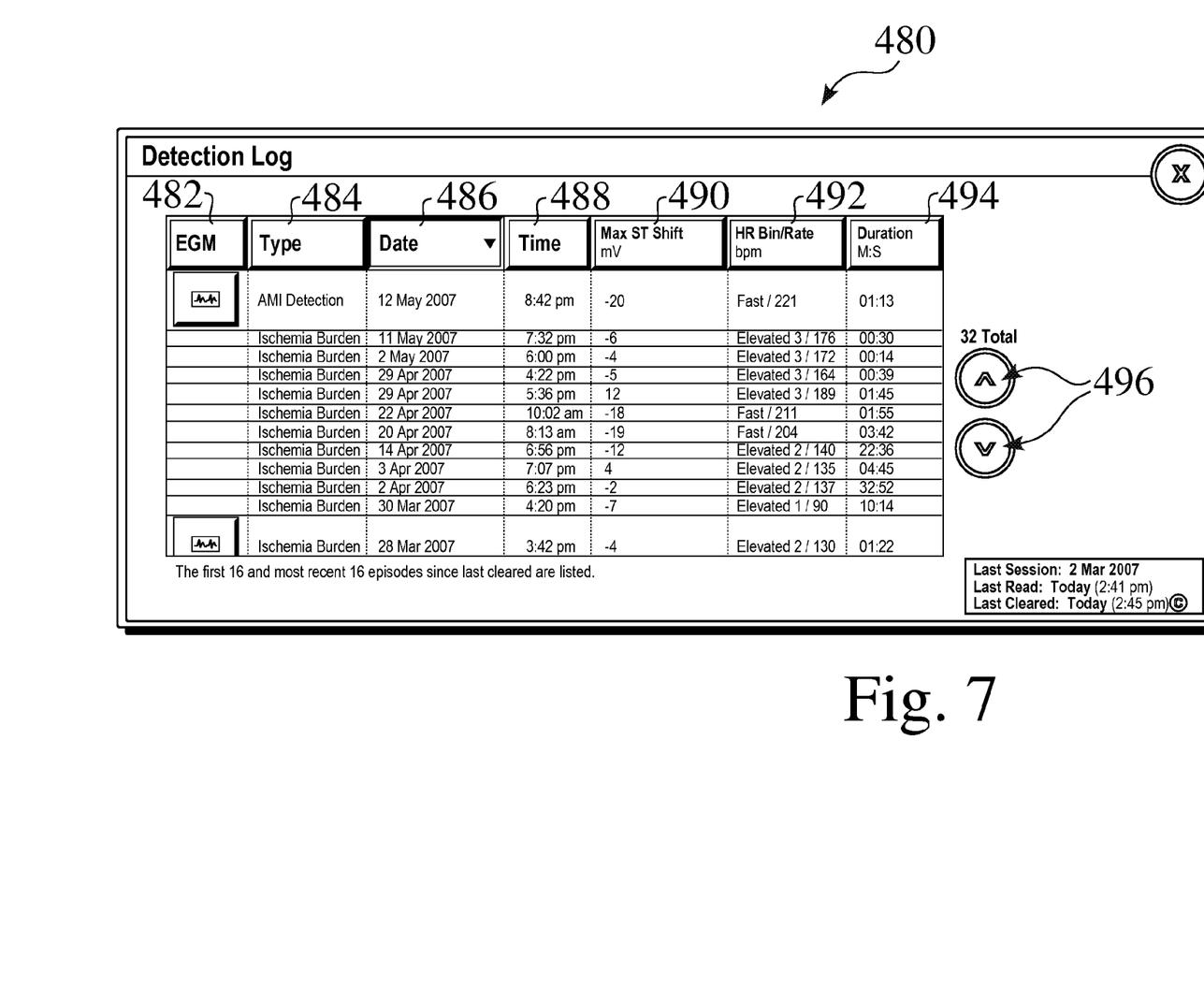
FIG. 7 illustrates a screen shot depicting a detailed ischemia burden detection log in accordance with an embodiment of the present invention.

FIG. 7 illustrates a screen shot 480 depicting a detection log 468 in accordance with an embodiment of the present invention. Screen shot 480 displays the most recent entries of coronary episodes (e.g., thirty-two). The coronary episodes may be ischemic episodes or AMI episodes (e.g., including major or minor ST elevation and depression). The detection log 468 includes a EGM 482 waveform for selected AMI and ischemic episodes, a classification of the type 484 of coronary episode, a date 486 when the episode occurred, the time 488 the episode occurred, a maximum ST shift 490 value in millivolts recorded at the time of the episode, a HR bin/Rate 492, and a duration 494 of the episode.

The HR bin/Rate 492 provides heart rate bins to categorize the heart rate at the time the ST segment occurred during the episode. The categories may include an elevated 1 bin, an elevated 2 bin, an elevated 3 bin, and a fast bin. Each bin has a range of heart rates. For example, elevated 1 bin includes a range of heart rates from 60 to 110 beats per min (bpm), elevated 2 bin includes heart rates from 110 to 150 bpm, elevated 3 bin includes heart rates from 150 to 200 bpm and the fast bin includes heart rates above 200 bpm. In addition, the HRbin/Rate 492 provides an average heart rate value in bpm based on calculating a statistical average from a set of heart beats (e.g., a set of six out of eight heart beats having ST segment variation). Alternatively, the heart rate provided may be the heart rate at the time of the detection of the onset of a coronary episode. In addition, a user may select from any one of the thirty-two recorded episodes by using the scroll buttons 496. However only ten of the most recent episodes will be displayed at one time.

Figure 8:
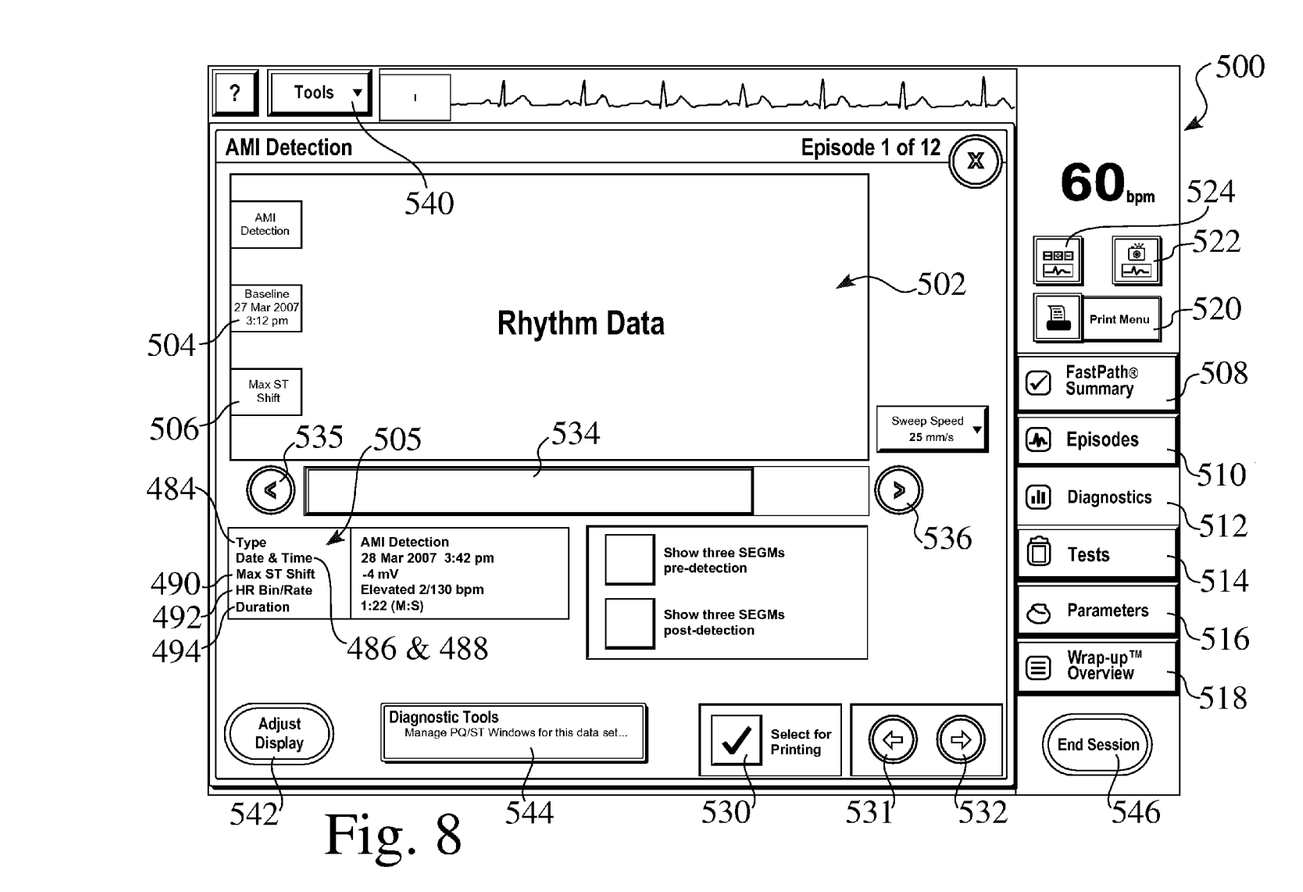
FIG. 8 illustrates a screen shot depicting a specific AMI episode and the corresponding cardiac waveforms in accordance with an embodiment of the present invention.

When a user selects to investigate a specific coronary episode, a new screen shot is displayed depicting the cardiac waveform that was recorded at the time of the episode and other cardiac information corresponding to the event. FIG. 8 illustrates a screen shot 500 depicting a selected AMI episode and FIG. 9 illustrates a screen shot 550 depicting a selected ischemic episode.

Figure 9:
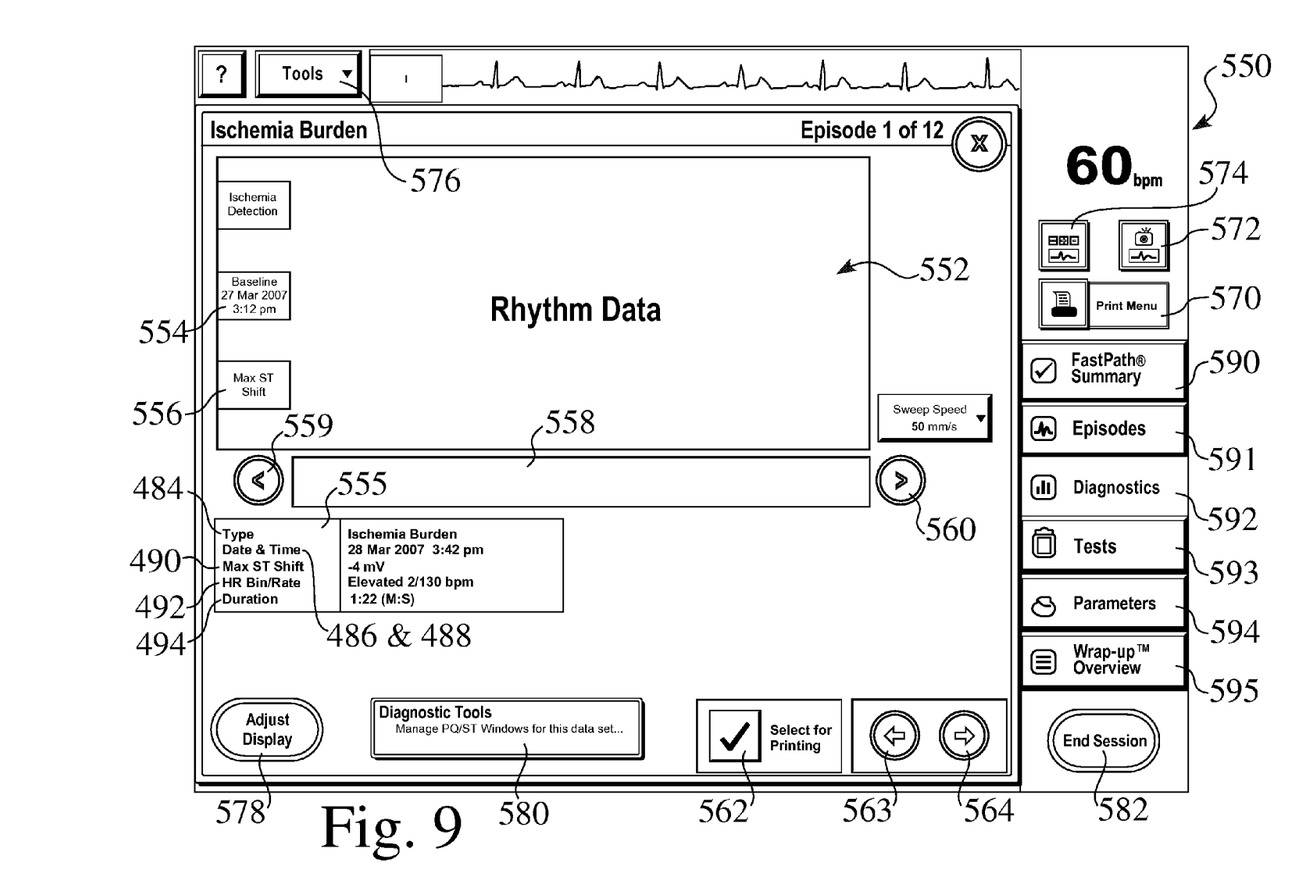
FIG. 9 illustrates a screen shot depicting a ischemia episode and the corresponding cardiac waveforms in accordance with an embodiment of the present invention.

FIG. 9 illustrates screen shot 550 depicting an ischemic episode and the corresponding cardiac waveform 552 in accordance with an embodiment of the present invention.

For example, when a user selects a particular ischemic episode from the detection log 480 (shown in FIG. 7), screen shot 550 will display the cardiac rhythm 552 that was recorded when the ischemic episode occurred. The cardiac rhythm 552 includes the time the baseline 554 was detected and the maximum ST shift 556. The user may scroll 558 the cardiac rhythm by using the left arrow 559 and right arrow 560. The screen shot 550 provides ischemic burden information 555 that repeats the information provided by the detection log 480 (shown in FIG. 7): the type 484 of episode, the date 486 and time 488 of the AMI occurrence, the maximum ST shift 490, the HR Bin/Rate 492, and the duration 494 of the episode The user also has the capability to display, view and print selected the ischemic episodes. For instance, when the user may select to print 562 after using the left arrow 563 and right arrow button 564 to scroll through the list of stored ischemic episodes and select particular cardiac rhythms 552 and the corresponding ischemic burden information 555. Other buttons provided by screen shot 550 include print menu 570, capture 572 the cardiac rhythm, magnify 574 the cardiac rhythm, tools 576, adjust display 578, diagnostic tools 580 and end session 582.

Screen shot 550 also contains buttons for the user to select a fastpath summary 590, episodes 591, diagnostics 592, tests 593, parameters 594, and wrap-up overview 595.

Improved methods and systems for trending acute coronary burden based on ST segment variations in an IEGM that are stored in an IMDs long term memory are provided. The method and system provide the capability to record long-term ischemia and AMI burden information by providing a detection log for storing: i) the most recent ischemic episodes; ii) the most recent AMI episodes; iii) the highest ST segment variation; iv) the longest ST segment variation; v) an episode type, and vi) a heart rate bin and an average heart rate at onset of the ischemic episode. In addition, a physician is able to interface with the ischemia and AMI burden information provided by using graphical user interfaces, such as screen shots that present trend information such as the method and system provide along with the trends associated therewith in using graphical user interfaces, such as screen shots that display an IEGM signal at a time of a coronary episode, co-display a baseline ST segment variation over a baseline period of time, and displaying over time, a percentage of time that coronary episodes occurred per unit of time as well as the count of coronary episodes that occurred per unit of time.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for trending ischemia burden for a patient, comprising:
    obtaining cardiac data over a period of time;
    collecting reference ST segments from the cardiac data;
    identifying onset and termination of multiple ischemia episodes based on ST segment variation between the reference ST segments and a measured ST segment within the cardiac data;
    analyzing the cardiac data associated with the multiple ischemia episodes to calculate ischemia burden information over the period of time, the ischemia burden information including at least one of:
        i) a count of the ischemia episodes over the period of time;
        ii) time durations of the ischemia episodes; and
        iii) a maximum ST segment variation for each of the multiple ischemia episodes over the period of time;
    recording the ischemia burden information; and
    presenting the ischemia burden information related to the multiple ischemia episodes as a multi-episode trend over the period of time.

2. The method of claim 1, wherein the ischemia burden information includes a detection log storing at least one of a) most recent ischemic episodes; b) highest ST segment variation; and c) longest ST segment variation.

3. The method of claim 1, wherein the ST segment variation represents a variation between one of a) reference and measured ST segment shifts and b) reference and measured ST segment deviations.

4. The method of claim 1, wherein the presenting includes displaying an IEGM signal at a time of a ischemia episode.

5. The method of claim 1, further comprising co-displaying, on a timeline, baseline ST segment variation over a baseline period of time and the ischemia burden information over the period of time.

6. The method of claim 1, further comprising storing an IEGM signal upon detecting onset of the ischemia episode.

7. The method according to claim 1, wherein the ischemia burden information includes at least one of:
    ii) the time durations of the ischemia episodes; and
    iii) the maximum ST segment variation for each of the ischemia episodes over the period of time.

8. A method for trending ischemia burden for a patient, comprising:
    obtaining cardiac data over a period of time;
    collecting reference ST segments from the cardiac data;
    identifying onset and termination of multiple ischemia episodes based on ST segment variation between the reference ST segments and a measured ST segment within the cardiac data;
    analyzing the cardiac data associated with the multiple ischemia episodes to calculate ischemia burden information over the period of time, the ischemia burden information including at least one of:
        i) a count of the ischemia episodes over the period of time;
        ii) time durations of the ischemia episodes; and
        iii) a maximum ST segment variation for each of the multiple ischemia episodes over the period of time;
    recording the ischemia burden information; and
    presenting the ischemia burden information related to the multiple ischemia episodes as a multi-episode trend over the period of time;
    wherein the presenting includes displaying a graphical representation, over time, of the ischemic burden information, where the graphical representation has one axis corresponding to time.

9. The method of claim 1, wherein the identifying includes statistically determining a variability between the measured ST segment and the reference ST segments for one of ST segment shift and ST segment deviation.

10. The method of claim 1, wherein the presenting includes displaying the multi-episode trend on a timeline as a percentage of time that ischemia episodes occurred per unit of time.

11. The method of claim 1, wherein the presenting includes displaying the multi-episode trend on a timeline as the count of ischemia episodes that occurred per unit of time.

12. A system for trending ischemia burden for a patient, comprising:
    a detector module configured to obtain cardiac data over a period of time, the detection module collecting reference ST segments from the cardiac data;
    a processor module configured to identify an onset and a termination of multiple ischemia episodes based on ST segment variation between the reference ST segments and a measured ST segment within the cardiac data; the processor module configured to analyze the cardiac data associated with the multiple ischemia episodes to calculate ischemia burden information over the period of time, the ischemia burden information including at least one of:
        i) a count of the ischemia episodes over the period of time;
        ii) time durations of the ischemia episodes; and
        iii) a maximum ST segment variation for each of the multiple ischemia episodes over the period of time;
    a memory module configured to record the ischemia burden information; and
    a display module configured to present the ischemia burden information related to the multiple ischemia episodes as a multi-episode trend over the period of time.

13. The system according to claim 12, wherein the ischemia burden information includes a detection log storing at least one of a) most recent ischemic episodes; b) highest ST segment variation; and c) longest ST segment variation.

14. The system according to claim 12, wherein the ST segment variation represents a variation between one of a) reference and measured ST segment shifts and b) reference and measured ST segment deviations.

15. The system according to claim 12, wherein the display module presents an IEGM signal at a time of a ischemia episode.

16. The system according to claim 12, wherein the display module co-displays, on a timeline, a baseline ST segment variation over a baseline period of time and the ischemia burden information over the period of time.

17. The system according to claim 12, wherein the memory module stores IEGM signal(s) upon detecting an onset of the ischemia episode.

18. The system according to claim 12, wherein the display module presents the multi-episode trend on a timeline as the count of ischemia episodes that occurred per unit of time.

19. The system according to claim 12, wherein the ischemia burden information includes at least one of:
  ii) the time durations of the ischemia episodes; and
  iii) the maximum ST segment variation for each of the ischemia episodes over the period of time.

20. A system for trending ischemia burden for a patient, comprising:
  a detector module configured to obtain cardiac data over a period of time, the detection module collecting reference ST segments from the cardiac data;
  a processor module configured to identify an onset and a termination of multiple ischemia episodes based on ST segment variation between the reference ST segments and a measured ST segment within the cardiac data; the processor module configured to analyze the cardiac data associated with the multiple ischemia episodes to calculate ischemia burden information over the period of time, the ischemia burden information including at least one of:
  i) a count of the ischemia episodes over the period of time;
  ii) time durations of the ischemia episodes; and
  iii) a maximum ST segment variation for each of the multiple ischemia episodes over the period of time;
  a memory module configured to record the ischemia burden information; and
  a display module configured to present the ischemia burden information related to the multiple ischemia episodes as a multi-episode trend over the period of time, wherein the display module presents a graphical representation, over time, of the ischemia burden information.

21. The system according to claim 12, wherein the detector module statistically determines a variability between the measured ST segment and the reference ST segments for one of ST segment shift and ST segment deviation.

22. The system according to claim 12, wherein the display module presents the multi-episode trend on a timeline as a percentage of time that ischemia episodes occurred per unit of time.

* * * * *